United States Patent
Arumugaswami et al.

(10) Patent No.: US 10,786,537 B2
(45) Date of Patent: Sep. 29, 2020

(54) METHOD OF INDUCING AN ONCOLYTIC EFFECT ON TUMOR CELLS USING ZIKA VIRUS

(71) Applicant: Cedars-Sinai Medical Center, Los Angeles, CA (US)

(72) Inventors: Vaithilingaraja Arumugaswami, Los Angeles, CA (US); Joshua Breunig, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/322,396

(22) PCT Filed: Aug. 17, 2017

(86) PCT No.: PCT/US2017/047295
§ 371 (c)(1),
(2) Date: Jan. 31, 2019

(87) PCT Pub. No.: WO2018/035294
PCT Pub. Date: Feb. 22, 2018

(65) Prior Publication Data
US 2019/0192593 A1   Jun. 27, 2019

Related U.S. Application Data

(60) Provisional application No. 62/376,689, filed on Aug. 18, 2016.

(51) Int. Cl.
*A61K 35/768*    (2015.01)
*A61P 35/00*    (2006.01)
*A61K 9/00*    (2006.01)

(52) U.S. Cl.
CPC .......... *A61K 35/768* (2013.01); *A61K 9/0019* (2013.01); *A61P 35/00* (2018.01); *C12N 2770/24132* (2013.01); *Y02A 50/391* (2018.01)

(58) Field of Classification Search
None
See application file for complete search history.

(56) References Cited

U.S. PATENT DOCUMENTS

| 2008/0152633 | A1* | 6/2008 | Suhrbier | C07K 14/005 |
| | | | | 424/93.21 |
| 2009/0081161 | A1 | 3/2009 | Roberts et al. | |
| 2012/0177701 | A1 | 7/2012 | Ilyinskii et al. | |
| 2015/0299271 | A1 | 10/2015 | Russell et al. | |
| 2016/0339064 | A1* | 11/2016 | Kovarik | A61K 35/74 |

FOREIGN PATENT DOCUMENTS

WO    2018035294  A1    2/2018

OTHER PUBLICATIONS

Rossi et al. Characterization of a Novel Murine Model to Study Zika Virus. Am. J. Trop. Med. Hyg., 94(6), 2016, pp. 1362-1369.*
Genbank: KU501215.1. Zika virus strain PRVABC59, complete genome. Dated Feb. 1, 2016.*
Zhu et al. Zika virus has oncolytic activity against glioblastoma stem cells. J. Exp. Med. 2017 vol. 214 No. 10 2843-2857.*
Chen et al. Treatment of Human Glioblastoma with a Live Attenuated Zika Virus Vaccine Candidate. mBio 9:e01683-18.*
Song et al. Inhibition of Retinoblastoma In Vitro and In Vivo with Conditionally Replicating Oncolytic Adenovirus H101. Invest Ophthalmol Vis Sci. 2010;51:2626-2635) DOI:10.1167/iovs.09-3516.*
International Search Report and Written Opinion of PCT/US2017/047295, dated Oct. 31, 2017, 10 Pages.
Hamel et al., Biology of Zika Virus Infection in Human Skin Cells, 2015, Journal of Virology, vol. 89(17), pp. 8880-8896.
Hughes et al., Infectivity of Immature Neurons to Zika Virus: A Link to Congenital Zika Syndrome, 2016, EBioMedicine, vol. 10, pp. 65-70.
Zhu et al., Comparative Genomic Analysis of Pre-Epidemic and Epidemic Zika Virus Strains for Virological Factors Potentially Associated with the Rapidly Expanding Epidemic, 2016, Emerging Microbes and Infections, vol. 5(3): e22, pp. 1-11.

* cited by examiner

*Primary Examiner* — Nianxiang Zou
(74) *Attorney, Agent, or Firm* — Linda B. Huber; Nixon Peabody LLP

(57) ABSTRACT

The present invention provide for methods of inducing an oncolytic effect on tumor cells using Zika virus. The invention also provides for inducing an oncolytic effect on brain tumors and treating brain tumors, and in particular, glioblastomas and neuroblastoma. The treatment involves the administration of Zika virus, which has an oncolytic effect on the tumor cells.

Figure 1A:
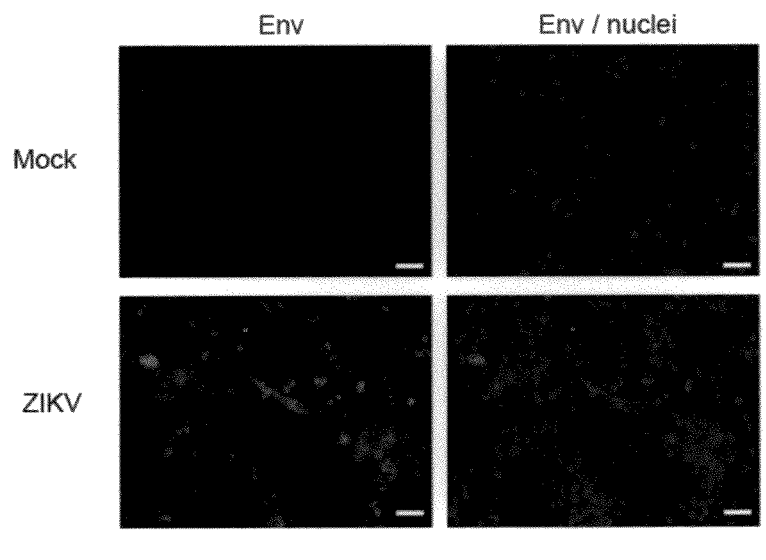
Figure 1A:
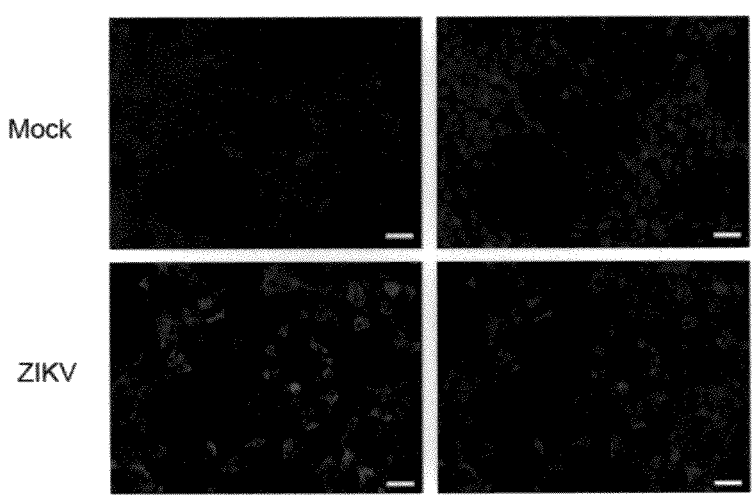

17 Claims, 4 Drawing Sheets
Specification includes a Sequence Listing.

METHOD OF INDUCING AN ONCOLYTIC EFFECT ON TUMOR CELLS USING ZIKA VIRUS

CROSS-REFERENCE TO RELATED APPLICATIONS

This application is a National Phase of International Application No. PCT/US2017/047295 filed Aug. 17, 2017, which designated the U.S. and that International Application was published under PCT Article 21(2) in English, which also includes a claim of priority under 35 U.S.C. § 119(e) to U.S. provisional patent application No. 62/376,689 filed Aug. 18, 2016, now expired, the entirety of which is hereby incorporated by reference.

FIELD OF INVENTION

This invention relates to oncolytic viral therapy, and particularly the treatment of glioblastoma.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Zika Virus (ZIKV) is a member of Flaviviridae family. It has emerged as a major human pathogen in the past year and is associated with causing fetal developmental defects (microcephaly), poor pregnancy outcomes and Guillain-Barre syndrome. Infected individuals, especially adults can be symptomless or present with mild symptoms such as fever, headache, rash, conjunctivitis, and joint/muscle pain. The virus was first isolated from a sentinel monkey in Uganda's Zika forest in 1947. Based on serological evidence, the first human case was reported in 1952. Zika viral-mediated tissue injury and host responses to infection are just becoming understood. Apoptotic cell death contributes to varied clinical manifestation of Flavivirus infections.

Gliomas are a type of brain tumor comprised of non-neuronal glial cells. Glioma accounts for 80% of all primary malignant brain tumors. Despite decades of research, patients with glioblastoma, the most common and deadly form of glioma, have a 5-year survival rate of 5.1%. Standard therapy for high-grade glioma requires a combination of surgical resection, radiation and chemotherapy. Though current therapy is aggressive, it offers little salvage for the patient's quality of life and survival. Due to the lack of effective therapy for high-grade glioma, it is imperative to explore therapeutics for this devastating disease. As such, there remains a desperate need in the art for methods of treating brain tumors, and especially, gliomas and glioblastomas.

SUMMARY OF THE INVENTION

The following embodiments and aspects thereof are described and illustrated in conjunction with compositions and methods which are meant to be exemplary and illustrative, not limiting in scope.

Various embodiments of the invention provide for a method of inducing an oncolytic effect on a tumor, comprising: administering a composition comprising a Zika virus to a subject in need thereof to induce the oncolytic effect on the tumor, wherein the tumor expresses a flaviviral cell entry receptor selected from the group consisting of GRP78, SDC2, HSP90AB1, TYRO2, AXL, MERTK and combinations thereof.

In various embodiments, the Zika virus can be an Asian genotype Zika virus. In various embodiments, the Asian genotype Zika virus can correspond to GenBank accession number KU501215 (clinical isolate PRVABC59). In various embodiments, the Zika virus can be an African genotype Zika virus.

In various embodiments, the tumor can be a brain tumor. In various embodiments, the tumor can be an ocular tumor. In various embodiments, the tumor can be retinoblastoma.

Various embodiments of the present invention provide for a method of treating a brain tumor, comprising: administering a composition comprising a Zika virus to a subject in need thereof to treat the brain tumor. In various embodiments, the method can further comprise providing the composition.

In various embodiments, the Zika virus can be an Asian genotype Zika virus. In various embodiments, the Asian genotype Zika virus can correspond to GenBank accession number KU501215 (clinical isolate PRVABC59). In various embodiments, the Zika virus is an African genotype Zika virus.

In various embodiments, the brain tumor can be glioma, glioblastoma, or neuroblastoma.

In various embodiments, administering the composition can comprise intra-tumoral delivery, intra-cerebral delivery, intracarotid delivery, or a combination thereof. In various embodiments, administering the composition can comprise intravenous delivery or subcutaneous delivery.

In various embodiments, the method can further comprise administering an additional brain tumor therapy.

Various embodiments of the present invention provide for a method of inducing an oncolytic effect on a brain tumor, comprising: administering a composition comprising a Zika virus to a subject in need thereof to induce the oncolytic effect on the brain tumor. In various embodiments, the method can further comprise providing the composition.

In various embodiments, the Zika virus can be an Asian genotype Zika virus. In various embodiments, the Asian genotype Zika virus can correspond to GenBank accession number KU501215 (clinical isolate PRVABC59). In various embodiments, the Zika virus can be an African genotype Zika virus.

In various embodiments, the brain tumor can be glioma, glioblastoma, or neuroblastoma.

In various embodiments, administering the composition can comprise intra-tumoral delivery, intra-cerebral delivery, intracarotid delivery, or a combination thereof. In various embodiments, administering the composition can comprise intravenous delivery or subcutaneous delivery.

In various embodiments, the method can comprise administering an additional brain tumor therapy.

Various embodiments provide for a composition, comprising: a Zika virus; and a pharmaceutically acceptable carrier. In various embodiments, the composition can further comprise a preservative. In various embodiments, the pharmaceutically acceptable carrier can also be a preservative. In various embodiments, the composition can be stored or provided at conditions that preserve effective amounts of the Zika virus.

Various embodiments of the present invention provide for a kit comprising: a composition a Zika virus and a pharmaceutically acceptable carrier; and instructions for administering the composition to a subject in need thereof to induce an oncolytic effect on a tumor expressing a flaviviral cell entry receptor selected from the group consisting of GRP78, SDC2, HSP90AB1, TYRO2, AXL, MERTK and combinations thereof. In various embodiments, the instructions can comprise administering the composition to a subject in need thereof to induce an oncolytic effect on a brain tumor, an ocular tumor, or reintoblastoma. In various embodiments, the instructions can comprise administering the composition to a subject in need thereof to treat a brain tumor, an ocular tumor, or an reintoblastoma.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 1A-1B depicts the productive infection of glioma cells by ZIKV in accordance to various embodiment of the present invention. (1A) Fluorescent microscopy images of ZIKV infected and uninfected (Mock) glioma cells are shown at 2 and 4 days postinfection (dpi). ZIKV multiplicity of infection (MOI) of 1 was used for infection. A pan-Flaviviral envelop antibody was used for specifically detecting ZIKV infected cells. (1B) Graph shows the ZIKV genome copies present in infected cells at 2 dpi. Genome copies were measured by RT-qPCR. (Scale bar 25 μm).

FIG. 2 depicts Zika viral infection of glioma tumoroid or tumor-spheroid culture in accordance with various embodiments of the present invention. Bright field (BF) and fluorescent microscopy images of uninfected (mock) and ZIKV infected U87 glioma tumoroid cultures at 2 dpi using MOI 1. A pan-Flaviviral envelope antibody was used for detecting ZIKV infected cells. (Scale bar 25 μm).

FIG. 3A-3C depicts oncolytic effect of ZIKV on Glioma cells in accordance with various embodiments of the present invention. (3A) Bright field images of ZIKV infected (MOI 5) and uninfected (mock) at 4 dpi. Note: In ZIKV infected culture mostly cell debris are seen. (3B) Graph shows the viability of ZIKV infected cells at 4 dpi using two different MOIs. (3C) Graph presents the caspase 3/7 activity measured in ZIKV infected and uninfected glioma cells. ZIKV infection causes an increase in apoptotic cell death.

FIG. 4A-4B shows that fetal and immortalized adult Retinal Pigment Epithelial (RPE) cells express specific RPE cell markers and Zika virus cellular co-factors for cell entry. (4A) Immunofluorescent images show expression of ZO-1 and RPE cell markers RPE65 and BEST1 (red) in fetal and adult RPE cells. Nuclei were stained with DAPI (blue). (4B) Graph shows the expression of various flaviviral entry receptors in fetal RPE cells (left), adult RPE cells (right), and iRSCs (center). Provided are the RT-qPCR Ct cycle values normalized to GAPDH expression. Note the Ct values are inversely related to the expression level of each receptor. The RPE cells express several ZIKV entry co-factors including AXL.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd *ed., Revised*, J. Wiley & Sons (New York, N.Y. 2006); March, *Advanced Organic Chemistry Reactions, Mechanisms and Structure* 7th *ed.*, J. Wiley & Sons (New York, N.Y. 2013); and Sambrook and Russel, *Molecular Cloning: A Laboratory Manual* 4th *ed.*, Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Therapeutically effective amount" as used herein refers to that amount which is capable of achieving beneficial results in a patient with a tumor; for example, a brain tumor. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

"Brain tumor" as used herein includes but are not limited to gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas.

ZIKV induces cell death in human neural progenitor cell-derived neurospheres and cerebral organoids, and in the brain of microcephalic newborn. Cell surface protein AXL has been shown to be a key viral entry receptor to various brain cell types. Zika virus has a higher preference for neural progenitor cells, thus, ZIKV infection is used herein as an oncolytic therapy for tumors, and particularly, brain tumors and ocular tumors, and more particularly, neuroblastomas, glioblastomas and retinoblastomas. Herein, we provide the first evidence of oncolytic nature of Zika virus towards human glioblastoma cancer.

As described herein, we observed that glioblastoma (GB) cells are efficiently infected by ZIKV, which resulted in massive cell death. 3-dimensional GB tumoroids robustly supported ZIKV infection. ZIKV infected GB cells underwent caspase 3/7-mediated apoptotic cell death. Taken together, for the first time, we provide evidence of oncolytic effect by ZIKV.

Various embodiments of the present invention are based, at least in part, on the findings as described in more detail herein.

Various embodiments of the present invention provide for a method of treating a brain tumor. The method comprises administering a composition comprising a Zika virus to a subject in need thereof. In various embodiments the method comprises providing a composition comprising a Zika virus; and administering the composition to a subject in need thereof.

In various embodiments, the virus is an Asian genotype Zika virus; for example, the Asian genotype Zika virus that corresponds to GenBank accession number KU501215 (clinical isolate PRVABC59). Other Asian genotype Zika viruses can be used as well.

In other embodiments, the virus is an African genotype Zika virus including, but not limited to the East African and West African sub-types.

"Genotype" used herein with reference with the Zika virus is also referred to as "lineage" and it is understood that the use of these terms with reference to the Zika virus is interchangeable.

In other embodiments, the virus is a Zika virus that corresponds to GenBank accession nos.: KU321639 (Brazil 2015 SPH2015), KJ776791 (French Polynesia H/PF/2013), KF383115 (Central African Republic ARB1362), KF383116 (Senegal 1968 ArD7117), KF383117 (Senegal 1997 ArD128000), KF383118 (Senegal 2001 ArD157995), KF383119 (Senegal 2001 ArD158084), KF268948 (CAR 1979 ARB13565), KF268949 (CAR 1980 ARB15076), KF268950 (CAR 1976 ARB7701), EU545988 (Yap 2007), KF993678 (Thailand 2013 PLCal_ZV), JN860885 (Cambodia 2010 FSS13025), HQ234499 (Malaysia 1966 P6-740), HQ234501 (Senegal 1984 ArD41519), HQ234500 (Nigeria 1968 IbH 30656), LC002520 (Uganda 1947 MR766), KU501215 (Puerto Rico PRVABC59), KU501216 (Guatemala 8375), or KU501217 (Guatemala 103344). (Lanciotti R S, Lambert A J, Holodniy M, Saavedra S, del Carmen Castillo Signor L. Phylogeny of Zika virus in Western Hemisphere, 2015 [letter]. Emerg Infect Dis. 2016 May. Available at http://dx.doi.org/10.3201/eid2205.160065, accessed on Aug. 17, 2016.)

In other embodiments, the virus is a Zika virus selected from Table 1 below. (Arunachalam Ramaiah, Lei Dai, Deisy Contreras, Sanjeev Sinha, Ren Sun, Vaithilingaraja Arumugaswami, Comparative analysis of protein evolution and RNA structural changes in the genome of pre-epidemic and epidemic Zika virus (2016) bioRxiv.)

TABLE 1

Zika viruses (1947-2016).

| Strain name | Accession number | Host | Year of isolation | Country | Genotype |
|---|---|---|---|---|---|
| MR 766 | AY632535 | Sentinel monkey | 1947 | Uganda | African lineage |
| MR 766 | DQ859059 | Sentinel monkey | 1947 | Uganda | African lineage |
| MR_766 | HQ234498 | Sentinel rhesus | 1947 | Uganda | African lineage |
| IbH_30656 | HQ234500 | *Homo sapiens* | 1968 | Nigeria | African lineage |
| ArD_41519 | HQ234501 | *Aedes africanus* | 1984 | Senegal | African lineage |
| ARB13565 | KF268948 | *Aedes africanus* | 1976 | CAR | African lineage |
| ARB15076 | KF268949 | *Aedes opok* | 1980 | CAR | African lineage |
| ARB7701 | KF268950 | *Aedes africanus* | 1976 | CAR | African lineage |
| ArB1362 | KF383115 | *Aedes africanus* | 1968 | CAR | African lineage |
| ArD7117 | KF383116 | *Aedes luteocephalus* | 1968 | Senegal | African lineage |
| ArD128000 | KF383117 | *Aedes luteocephalus* | 1997 | Senegal | African lineage |
| ArD157995 | KF383118 | *Aedes dalzieli* | 2001 | Senegal | African lineage |
| ArD158084 | KF383119 | *Aedes dalzieli* | 2001 | Senegal | African lineage |
| ArD142623 | KF383120 | *Anopheles coustani* | 2000 | Senegal | African lineage |
| MR 766 | KU720415 | Sentinel monkey | 1947 | Uganda | African lineage |
| MR766-NIID | LC002520 | Sentinel monkey | 1947 | Uganda | African lineage |
| MR 766 | NC_012532 | Sentinel monkey | 1947 | Uganda | African lineage |
| ArD158095 | KF383121 | | | | African lineage |
| EC_Yap | EU545988 | *Homo sapiens* | 2007 | Micronesia | Asian lineage |
| P6-740 | HQ234499 | *Aedes aegypti* | 1966 | Malaysia | Asian lineage |
| FSS13025 | JN860885 | *Homo sapiens* | 2010 | Cambodia | Asian lineage |
| PLCal_ZV | KF993678 | *Homo sapiens* | 2013 | Canada | Asian lineage |
| H/PF/2013 | KJ776791 | *Homo sapiens* | 2013 | French Polynesia | Asian lineage |
| Z1106033 | KU312312 | *Homo sapiens* | 2015 | Suriname | Asian lineage |
| ZikaSPH2015 | KU321639 | *Homo sapiens* | 2015 | Brazil | Asian lineage |
| BeH818995 | KU365777 | *Homo sapiens* | 2015 | Brazil | Asian lineage |
| BeH819015 | KU365778 | *Homo sapiens* | 2015 | Brazil | Asian lineage |
| BeH819966 | KU365779 | *Homo sapiens* | 2015 | Brazil | Asian lineage |
| BeH815744 | KU365780 | *Homo sapiens* | 2015 | Brazil | Asian lineage |
| Brazil-ZKV2015 | KU497555 | *Homo sapiens* | 2015 | Brazil | Asian lineage |
| PRVABC59 | KU501215 | *Homo sapiens* | 2015 | Puerto Rico | Asian lineage |
| 103344 | KU501216 | *Homo sapiens* | 2015 | Guatemala | Asian lineage |
| 8375 | KU501217 | *Homo sapiens* | 2015 | Guatemala | Asian lineage |

TABLE 1-continued

Zika viruses (1947-2016).

| Strain name | Accession number | Host | Year of isolation | Country | Genotype |
|---|---|---|---|---|---|
| Haiti/1225/2014 | KU509998 | *Homo sapiens* | 2014 | Haiti | Asian lineage |
| Natal RGN | KU527068 | *Homo sapiens* | 2015 | Brazil | Asian lineage |
| SSABR1 | KU707826 | *Homo sapiens* | 2015 | Brazil | Asian lineage |
| VE_Ganxian | KU744693 | *Homo sapiens* | 2016 | China | Asian lineage |
| GDZ16001 | KU761564 | *Homo sapiens* | 2016 | China | Asian lineage |
| MRS_OPY_Martinique_PaRi_2015 | KU647676 | *Homo sapiens* | 2015 | Martinique | Asian lineage |
| tc/THA/2014/SV01 27-14 | KU681081 | *Homo sapiens* | 2014 | Thailand | Asian lineage |
| tc/PHL/2012/CPC-0740 | KU681082 | *Homo sapiens* | 2012 | Philippines | Asian lineage |
| BeH823339 | KU729217 | *Homo sapiens* | 2015 | Brazil | Asian lineage |
| BeH828305 | KU729218 | *Homo sapiens* | 2015 | Brazil | Asian lineage |
| GD01 | KU740184 | *Homo sapiens* | 2016 | China | Asian lineage |
| FLR | KU820897 | *Homo sapiens* | 2015 | Colombia | Asian lineage |
| ZJ03 | KU820899 | *Homo sapiens* | 2016 | China | Asian lineage |

In various embodiments, the brain tumor treated is glioma, glioblastoma, glioblastoma multiforme (GBM), oligodendroglioma, primitive neuroectodermal tumor, low, mid and high grade astrocytoma, ependymoma (e.g., myxopapillary ependymoma papillary ependymoma, subependymoma, anaplastic ependymoma), oligodendroglioma, medulloblastoma, meningioma, pituitary adenoma, neuroblastoma, or craniopharyngioma. In particular embodiments, the brain tumor treated is a glioblastoma, or neuroblastoma.

In various embodiments, the subject in need thereof is a subject who has been diagnosed with a brain tumor or is suspected of having a brain tumor.

In various embodiments, the composition comprising the Zika virus comprises about 10e3 to 10e11 (log scale) viral particles (VP). In various embodiments, the composition comprising the Zika virus comprises about 10e4 to 10e11 (log scale) viral particles (VP). In various embodiments, the quantity of Zika virus is about 10e3, 10e4, 10e5, 10e6, 10e7, 10e8, 10e9, 10e10, or 10e11. The actual quantity of viral particles can depend on the tumor volume or estimated tumor volume. For example, tumor volumes of in the about 1 cm$^3$ can be treated with about 10e3 to 10e9 viral particles and tumor volumes of about 100 cm$^3$ can be treated with about 10e6 to 10e11 viral particles.

In various embodiments, the composition comprising the Zika virus comprises a quantity of viral particles for a multiplicity of infection (MOI) of 1, 2, 3, 4, 5, 10, 25, 50 or 100, or about 1, 2, 3, 4, 5, 10, 25, 50, or 100.

Various embodiments of the present invention provide for a method of inducing an oncolytic effect on a brain tumor, comprising: administering a composition comprising a Zika virus to a subject in need thereof. In various embodiments, the method of inducing an oncolytic effect on a brain tumor, comprises: providing the composition comprising a Zika virus and administering the composition to a subject in need thereof.

In various embodiments, the Zika virus is an Asian genotype Zika virus. In various embodiments, the Asian genotype Zika virus corresponds to GenBank accession number KU501215 (clinical isolate PRVABC59). Other Asian genotype Zika viruses can be used as well.

In other embodiments, the virus is an African genotype Zika virus including, but not limited to the East African and West African sub-types.

In other embodiments, the virus is a Zika virus that corresponds to GenBank accession nos.: KU321639 (Brazil 2015 SPH2015), KJ776791 (French Polynesia H/PF/2013), KF383115 (Central African Republic ARB1362), KF383116 (Senegal 1968 ArD7117), KF383117 (Senegal 1997 ArD128000), KF383118 (Senegal 2001 ArD157995), KF383119 (Senegal 2001 ArD158084), KF268948 (CAR 1979 ARB13565), KF268949 (CAR 1980 ARB15076), KF268950 (CAR 1976 ARB7701), EU545988 (Yap 2007), KF993678 (Thailand 2013 PLCal_ZV), JN860885 (Cambodia 2010 FSS13025), HQ234499 (Malaysia 1966 P6-740), HQ234501 (Senegal 1984 ArD41519), HQ234500 (Nigeria 1968 IbH 30656), LC002520 (Uganda 1947 MR766), KU501215 (Puerto Rico PRVABC59), KU501216 (Guatemala 8375), or KU501217 (Guatemala 103344). (Lanciotti R S, Lambert A J, Holodniy M, Saavedra S, del Carmen Castillo Signor L. Phylogeny of Zika virus in Western Hemisphere, 2015 [letter]. Emerg Infect Dis. 2016 May. Available at http://dx.doi.org/10.3201/eid2205.160065, accessed on Aug. 17, 2016.)

In other embodiments, the virus is a Zika virus selected from Table 1 above.

In various embodiments, the brain tumor in which the oncolytic effect is induced is glioma, glioblastoma, glioblastoma multiforme (GBM), oligodendroglioma, primitive neuroectodermal tumor, low, mid and high grade astrocytoma, ependymoma (e.g., myxopapillary ependymoma papillary ependymoma, subependymoma, anaplastic ependymoma), oligodendroglioma, medulloblastoma, meningioma, pituitary adenoma, neuroblastoma, or craniopharyngioma. In particular embodiments, the brain tumor in which the oncolytic effect is induced is a glioblastoma, or neuroblastoma.

In various embodiments, the subject in need thereof is a subject who has been diagnosed with a brain tumor or is suspected of having a brain tumor.

In various embodiments, the composition comprising the Zika virus comprises about 10e3 to 10e11 (log scale) viral particles (VP). In various embodiments, the composition comprising the Zika virus comprises about 10e4 to 10e11 (log scale) viral particles (VP). In various embodiments, the quantity of Zika virus is about 10e3, 10e4, 10e5, 10e6, 10e7, 10e8, 10e9, 10e10, or 10e11. The actual quantity of viral particles can depend on the tumor volume or estimated tumor volume. For example, tumor volumes of in the about 1 cm$^3$ can be treated with about 10e3 to 10e9 viral particles and tumor volumes of about 100 cm$^3$ can be treated with about 10e6 to 10e11 viral particles.

In various embodiments, the composition comprising the Zika virus comprises a quantity of viral particles for a multiplicity of infection (MOI) of 1, 2, 3, 4, 5, 10, 25, 50 or 100, or about 1, 2, 3, 4, 5, 10, 25, 50, or 100.

Various embodiments provide for a method of inducing an oncolytic effect on a tumor, comprising: administering a composition comprising a Zika virus to a subject in need thereof, wherein the tumor expresses a flaviviral cell entry receptor selected from the group consisting of GRP78, SDC2, HSP90AB1, TYRO2, AXL, MERTK and combinations thereof. In various embodiments, the tumor highly expresses a flaviviral cell entry receptor selected from the group consisting of GRP78, SDC2, HSP90AB1, TYRO2, AXL, MERTK and combinations thereof relative to non-tumor cells. In various embodiments, the tumor equally or substantially equally expresses a flaviviral cell entry receptor selected from the group consisting of GRP78, SDC2, HSP90AB1, TYRO2, AXL, MERTK and combinations thereof relative to non-tumor cells. Some instances the expression level of entry receptors may be similar for both tumor and normal cells. However, there can be differences in other intra-cellular co-factors supporting ZIKV replication, which can influence outcome. In various embodiments, the flaviviral cell entry receptor is AXL. Examples of co-factors that can be expressed in various types of tumor cells include but are not limited to DC-SIGN, MRC1, RPSA, PHB, TIM1, TIM3, ITGAV, ITGA5, ITGB3, SCARB1, and NCR2. Additional examples of co-factors are in FIG. 4B.

In various embodiments, the tumor expresses flaviviral cell entry receptor GRP78, SDC2, HSP90AB1, TYRO2, AXL, MERTK or combinations thereof at least 1.1-fold, 1.5-fold, 2-fold, 3-fold, 4-fold, 5-fold, 6-fold, 7-fold, 8-fold, 9-fold, or 10-fold higher than non-tumor cells. In various embodiments, the tumor expresses flaviviral cell entry receptor GRP78, SDC2, HSP90AB1, TYRO2, AXL, MERTK or combinations thereof at least 10-fold, 20-fold, 30-fold, 40-fold, 50-fold, 60-fold, 70-fold, 80-fold, 90-fold or 100-fold higher than non-tumor cells.

Examples of tumors that express a flaviviral cell entry receptor (e.g., GRP78, SDC2, HSP90AB1, TYRO2, AXL, MERTK or combinations thereof), include but are not limited to: skin cancers (e.g., basal cell carcinoma, squamous cell carcinoma, melanoma, Merkel cell carcinoma, atypical fibroxanthoma, cutaneous lymphoma, and dermatofibrosarcoma), lung cancers (e.g., small cell lung cancers (SCLC) and non-small cell lung cancers (NSCLC)) and gastrointestinal cancers (e.g., esophageal cancer (carcinoma), stomach cancer (gastric cancer), liver cancer (hepatocellular carcinoma), pancreatic cancer and colorectal cancers.)

While not wishing to be bound by any particular theory, the inventors believe that tumors that express one or more of these flaviviral cell entry receptors allow for preferential entry of the Zika virus. The Zika virus subsequently triggers apoptosis or programmed cell death in the tumor cell, or induces activation of cellular innate and inflammatory genes leading to induction of inflammatory and immune responses against the tumor or cancerous tumor.

In various embodiments, the Zika virus is an Asian genotype Zika virus. In various embodiments, the Asian genotype Zika virus corresponds to GenBank accession number KU501215 (clinical isolate PRVABC59). Other Asian genotype Zika viruses can be used as well.

In other embodiments, the virus is an African genotype Zika virus including, but not limited to the East African and West African sub-types.

In other embodiments, the virus is a Zika virus that corresponds to GenBank accession nos.: KU321639 (Brazil 2015 SPH2015), KJ776791 (French Polynesia H/PF/2013), KF383115 (Central African Republic ARB1362), KF383116 (Senegal 1968 ArD7117), KF383117 (Senegal 1997 ArD128000), KF383118 (Senegal 2001 ArD157995), KF383119 (Senegal 2001 ArD158084), KF268948 (CAR 1979 ARB13565), KF268949 (CAR 1980 ARB15076), KF268950 (CAR 1976 ARB7701), EU545988 (Yap 2007), KF993678 (Thailand 2013 PLCal_ZV), JN860885 (Cambodia 2010 FSS13025), HQ234499 (Malaysia 1966 P6-740), HQ234501 (Senegal 1984 ArD41519), HQ234500 (Nigeria 1968 IbH 30656), LC002520 (Uganda 1947 MR766), KU501215 (Puerto Rico PRVABC59), KU501216 (Guatemala 8375), or KU501217 (Guatemala 103344). (Lanciotti R S, Lambert A J, Holodniy M, Saavedra S, del Carmen Castillo Signor L. Phylogeny of Zika virus in Western Hemisphere, 2015 [letter]. Emerg Infect Dis. 2016 May. Available at http://dx.doi.org/10.3201/eid2205.160065, accessed on Aug. 17, 2016.)

In other embodiments, the virus is a Zika virus selected from Table 1 above.

Figure 4A:
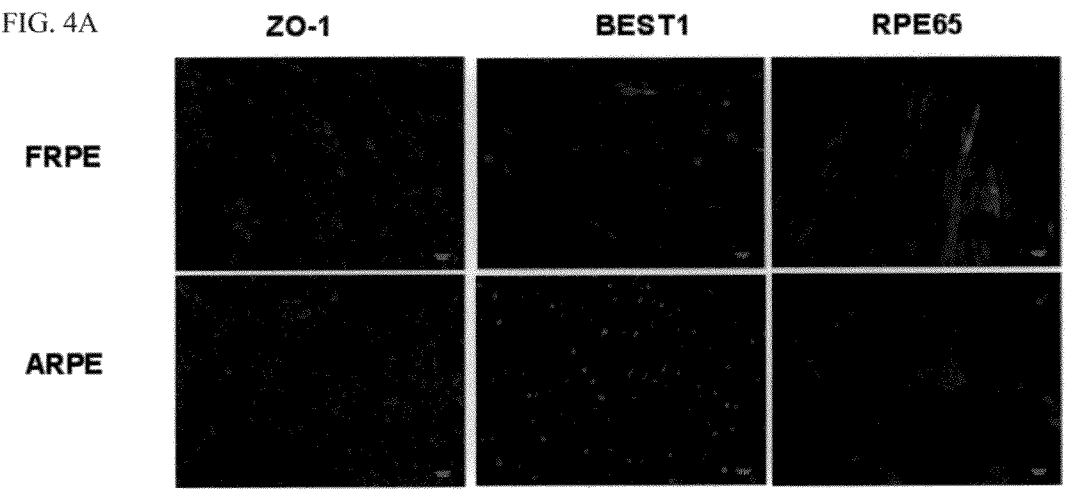
Figure 4B:
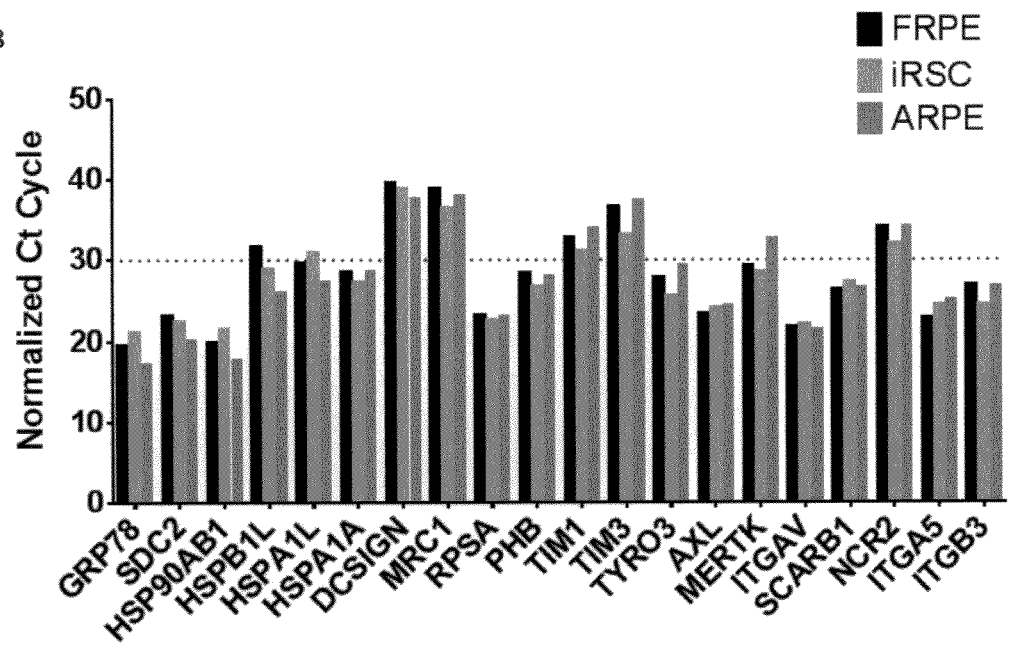

In various embodiments, the tumor in which the oncolytic effect is induced is an ocular tumor; for example, retinoblastoma. Immortalized adult Retinal Pigment Epithelial (ARPE) cells and fetal RPE (FRPE) cells expressed several flaviviral cell entry receptors GRP78, SDC2, HSP90AB1, TYRO3, AXL, and MERTK (FIG. 4A-4B). Cancers arising from ocular tissues such as retinoblastoma can be killed by oncolytic Zika viruses.

In various embodiments, the subject in need thereof is a subject who has been diagnosed with a tumor that expresses flaviviral cell entry receptor GRP78, SDC2, HSP90AB1, TYRO2, AXL, MERTK or combinations thereof. In various embodiments, the subject in need thereof is a subject who has been diagnosed with a tumor that expresses the flaviviral cell entry receptor AXL. In various embodiments, the subject in need thereof is a subject who has been diagnosed with an ocular tumor. In various embodiments, the subject in need thereof is a subject who has been diagnosed with retinoblastoma. In various embodiments, the subject in need thereof is a subject who has been diagnosed with a brain tumor.

In various embodiments, the composition comprising the Zika virus comprises about 10e3 to 10e11 (log scale) viral particles (VP). In various embodiments, the composition comprising the Zika virus comprises about 10e4 to 10e11 (log scale) viral particles (VP). In various embodiments, the quantity of Zika virus is about 10e3, 10e4, 10e5, 10e6, 10e7, 10e8, 10e9, 10e10, or 10e11. The actual quantity of viral particles can depend on the tumor volume or estimated tumor volume. For example, tumor volumes of in the about 1 cm$^3$ can be treated with about 10e3 to 10e9 viral particles and tumor volumes of about 100 cm$^3$ can be treated with about 10e6 to 10e11 viral particles.

In various embodiments, the composition comprising the Zika virus comprises a quantity of viral particles for a multiplicity of infection (MOI) of 1, 2, 3, 4, 5, 10, 25, 50, or 100 or about 1, 2, 3, 4, 5, 10, 25, 50, or 100.

Routes of Administration

In various embodiments, the pharmaceutical compositions comprising a Zika virus according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

In some embodiments, the Zika virus is administered via intra-tumoral delivery at a single site or multiple sites. In some embodiments, the Zika virus is administered via intra-cerebral delivery. In other embodiments, the Zika virus is administered intravenously or subcutaneously. In other embodiments, the Zika virus is administered via intracarotid delivery. In other embodiments, the Zika virus is administered via delivery to a body cavity, intraperitoneally. In other embodiments the Zika virus is administered via intranasal delivery. In other embodiments, the Zika virus is administered via oral delivery. In other embodiments, the Zika virus is administered via intra-rectal delivery. In other embodiments, the Zika virus is administered via intra-colon delivery. In other embodiments, the Zika virus is administered via ocular delivery.

Pharmaceutical Compositions

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In some embodiments, the pharmaceutical compositions comprise one or more agents to preserve the virus. In some embodiments, the pharmaceutically acceptable carrier will also serve as the preservative. It will be appreciated that for the pharmaceutical compositions comprising the virus to maintain its ability to be effective, effective amounts of the virus in the composition needs to be kept alive, and thus, a preservative can be used to achieve this purpose.

In some embodiments, the pharmaceutical compositions are stored and/or provided at conditions that preserve effective amounts of the virus; for example, at lower temperatures.

The pharmaceutical compositions according to the invention can also be encapsulated, tableted or prepared in an emulsion or syrup for oral administration. The pharmaceutical compositions according to the invention can also be used for preparation of the composition for parenteral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

In various embodiments, the carriers can be saline, phosphate buffered saline, or lipids.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of an effective oncolytic Zika virus can be indicated to the skilled artisan by the in vitro responses or responses in animal models. Such dosages typically can be reduced by up to about one order of magnitude in concentration or amount without losing the relevant biological activity. Thus, the actual dosage can depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

Kits

The present invention is also directed to a kit to treat brain tumors such as gliomas and glioblastomas. The kit is useful for practicing the inventive method of treating brain tumors. The kit is an assemblage of materials or components, including at least one of the inventive compositions. Thus, in some embodiments the kit contains a composition including a Zika virus as described above.

The exact nature of the components configured in the inventive kit depends on its intended purpose. For example, some embodiments are configured for the purpose of treating brain tumors such as glioma and glioblastomas. Other embodiments are configured for the purpose of treating inducing an oncolytic effect on a tumor/cancer, such as a brain tumor, an ocular tumor, skin cancer, gastrointestinal cancer, and lung cancer. In one embodiment, the kit is configured particularly for the purpose of treating or inducing an oncolytic effect on mammalian subjects. In another embodiment, the kit is configured particularly for the purpose of treating or inducing an oncolytic effect on human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat brain tumors such as glioma and glioblastomas, or to induce an oncolytic effect on a tumor. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in tumor treatment and/or administration of viral particles. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a Zika virus. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Cells.

U-87 MG cell line (human glioblastoma; astrocytoma; classified as grade IV) was purchased from the American Type Culture Collection (ATCC, USA) and was maintained using complete Eagle's Minimum Essential Medium (EMEM) (Fisher Scientific). Complete EMEM was supplemented with 10% fetal bovine serum (FBS), penicillin (100 units/ml), and streptomycin (100 mg/ml) (Life Technologies). The cells were maintained at 37° C. with 5% $CO_2$ and were passage every third day using 1× trypsin with EDTA.

Zika Virus.

An Asian genotype, clinical isolate PRVABC59 (GenBank accession number KU501215) was utilized in this study. Early passage PRVABC59 Zika virus was obtained from Centers for Disease Control and Prevention (CDC). The original ZIKV stock (P=3) was subjected to additional 2 passages in Vero cells to generate working viral stock. Viral titer was measured by plaque assay as described previously.

Zika Viral Infection.

Glioblastoma cells were seeded at a density of $3\times10^4$ cells per well in a 48-well plate ($1.5\times10^4$ cells per well of 96-well plate). The next day, a Zika viral inoculum was prepared in a serum-free base media at a Multiplicity of Infection (MOI) of 1 or 5. 200 μL (100 μL per well of 96-well plate) of viral inoculum was added to each well and the inoculated plates were incubated in 37° C. with 5% $CO_2$ for 2-4 hrs. At the end of incubation, the inoculum was replaced with 10% FBS supplemented media. For the mock infection control, the cells received only basic media that was used for preparing the viral inoculum. This mock or uninfected control cells were included for each time point for comparison. At the indicated time points, samples were collected for various assays, including immunofluorescence assay, cell viability assay, caspase 3/7 assay and reverse transcription quantitative PCR (RT-qPCR).

Caspase 3/7 Activity Assay for Apoptosis Measurement.

Caspase-Glo 3/7 Assay (Promega, USA) was performed as per the manufacturer's protocol. At indicated time points, Zika virus infected and control mock infected cells in the 96-well plate were incubated with the proluminescent caspase-3/7 substrate for 1 hour at room temperature. Subsequently, 100 μL of lysate was transferred to a white 96 well microtiter plate for reading the luminescence signal using a luminometer (Glomax Microplate Luminometer, Promega).

Cell Viability Assay.

CellTiter-Glo Luminescent assay (Promega, USA) to measure intracellular ATP content was performed as per the manufacturer's protocol. At indicated time points, Zika virus infected and control mock infected cells in the 96-well plate were incubated with the substrate for 1 hour at room temperature. Subsequently, 100 μL of lysate was transferred to a white 96 well microtiter plate for reading the luminescence signal using a luminometer (Glomax Microplate Luminometer, Promega).

Reverse Transcription Quantitative PCR Analysis.

Total RNA was extracted from mock and infected glioma cells at the designated time points using an RNeasy Mini Kit (QIAGEN). After treatment with RNase-free DNase, 1 μg of RNA was reverse-transcribed into cDNA using random hexamer primer and the SuperScript III Reverse Transcriptase Kit (Life Technologies) as recommended by the manufacturer. The following conditions were used for cDNA amplification: 65° C. for 5 min; 4° C. for 1 min followed by 55° C. for 60 min and 72° C. for 15 min. Quantitative real-time PCR was carried out using Platinum SYBR Green qPCR SuperMix-UDG with ROX Kit (Life Technologies) by the QuantStudio™ 12K Flex Real-Time PCR System (Life Technologies). Known copy numbers (from 10e0 to 10e10) of ZIKV gene template were included as a standard. The relative concentration of each transcript was calculated using $2^{-\Delta CT}$ method using Glyceraldehyde 3-phosphate dehydrogenase (GAPDH) threshold cycle ($C_T$) values for normalization. The normalized $C_T$ values were used for calculating copy numbers. The qPCR primer pairs for the mRNA transcript targets are given in Table 2. The following conditions were used for transcript amplification: 50° C. for 2 min; 95° C. for 2 min followed by 40 cycles of 95° C. for 15 sec and 60° C. for 1 min.

TABLE 2

List of primers used in this study.

| Gene | Forward primer sequence (5'-3') | SEQ ID NO: | Revers primer sequence (5'-3') | SEQ ID NO: |
|---|---|---|---|---|
| GAPDH | CCACCTTTGACGCTGGG | 1 | CATACCAGGAAATG AGCTTGACA | 2 |
| ZIKV | AARTACACATACCARA ACAAAGTGGT | 3 | TCCRCTCCCYCTYT GGTCTTG | 4 |

R can be A or G; Y can be C or T

Immunofluorescence Assay.

Immunofluorescence assay was performed on both the mock and infected Vero cells fixed with methanol. The fixed cells were incubated at −20° C. for 30 min., then washed three times with 1× PBS. Following three PBS washes, the cells were permeabilized and blocked with 10% fetal bovine serum, 3% BSA, 0.1% Triton-x 100 in PBS. Subsequently, the fixed and permeabilized cells were incubated with mouse monoclonal antibody for Flavivirus group antigen [D1-4G2-4-15 (4G2)] (Absolute Antibody Ltd.) at a 1:200 dilution for up to 6 hrs or overnight incubation at 4° C. The secondary antibodies, goat anti-mouse polyclonal antibody (Alexa fluor 488) (Life Technologies, USA) were added at 1:1000 dilutions and incubated for 1 hr at room temperature. Between antibody changes the cells were washed five times with PBS. The nuclei were stained with the addition of 4',6-diamidino-2-phenylindole (DAPI) (Life Technologies, USA).

Statistical Analysis.

There were a total of three independent biological replicates that were carried out for each of the represented experiments in the study. The error bars in the graph reflect the standard deviation. P-values were determined by the two-tailed student's t-test and significance was reported if the p value is $p<0.05$ (*); $p<0.001$ (); $p<0.0001$ (*).

Glioblastoma Cells Support Robust ZIKV Infection.

Figure 1B:
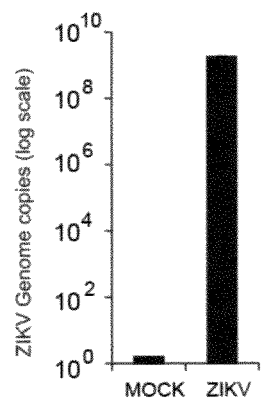

To evaluate the susceptibility of glioblastoma cells to Zika virus infection, we utilized an in vitro infectious cell culture system based on U-87 cell line (grade IV glioblastoma). We used a viral MOI of 1 for this experiment. At 2 days post-infection (dpi) and 4 dpi, the establishment of active viral infection was confirmed by immunocytochemistry analysis of ZIKV infected cells using an antibody recognizing flaviviral envelope (Env) protein. (FIG. 1A). We verified the genome replication of Zika virus in glioblastoma cells at indicated time points using RT-qPCR (FIG. 1B). At 2 dpi, we observed several log increase in the viral genome copy level compared to uninfected cells. These results indicate glioblastoma cells are susceptible to ZIKV replication.

ZIKV Infection of Glioblastoma 3-Dimensional Tumoroids.

Figure 2:
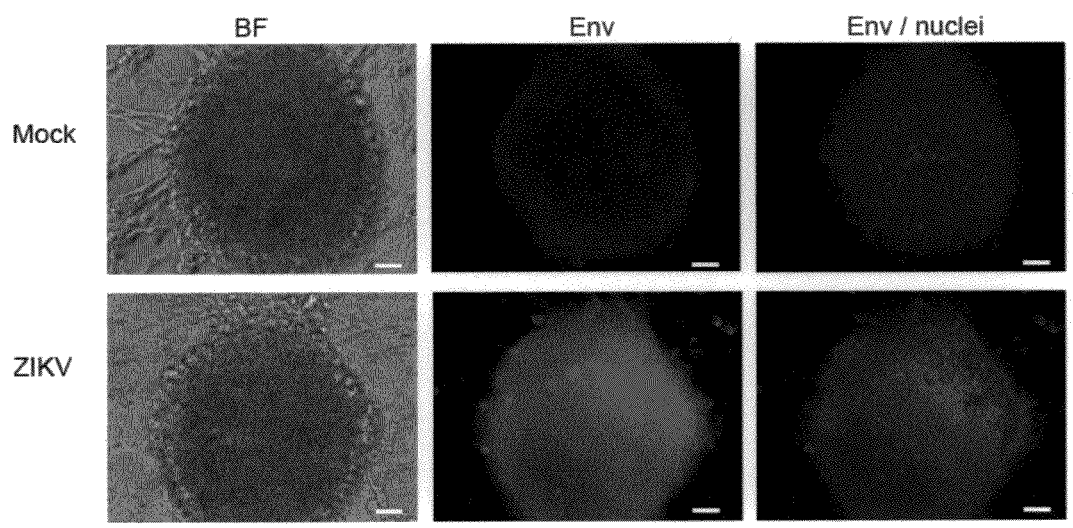

The U-87 cells formed spontaneous 3-D aggregates of tumoroids while culturing on regular 96- or 48-well plates. Immunofluorescent staining indicated the tumoroid cells were heavily infected by ZIKV (FIG. 2). This observation suggests that the glioblastoma cancers can be efficiently infected with ZIKV.

Oncolytic Effect of Zika Virus.

Figure 3A:
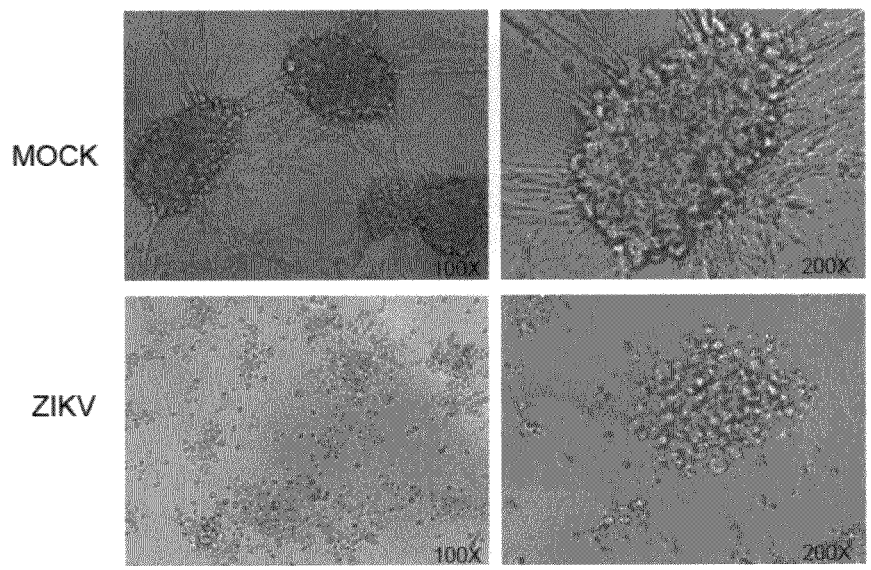
Figure 3B:
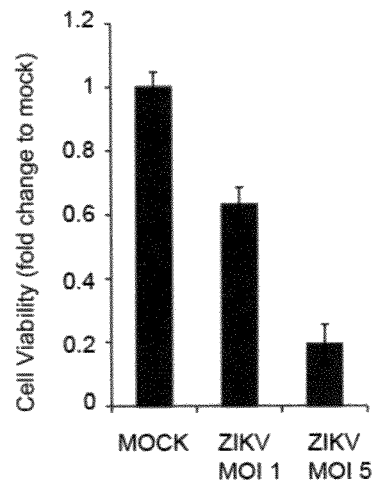
Figure 3C:
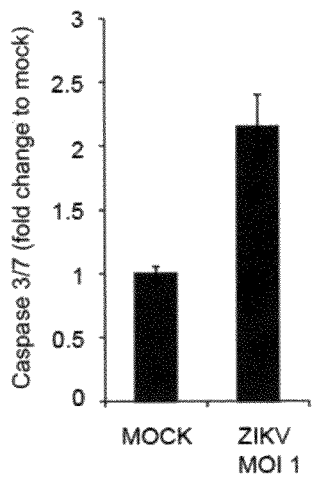

By 4 dpi, we observed obvious ZIKV-mediated cytopathic effect of infected glioblastoma cells. Infected cells were rounded up and easily detached. Mainly cellular debris was found in the ZIKV infected wells (FIG. 3A), where us uninfected cells were viable and formed tumoroids and filamentous cellular networks. Cell viability assay measuring ATP content showed that ZIKV infected cells at both MOI 1 and 5 had significantly reduced viability compared to that of uninfected cells (FIG. 3B). Virus infection can trigger apoptosis or programmed cell death. Programmed cell death is executed by intracellular cysteine proteases caspase-3, caspase-6 and caspase-7. The ZIKV infected cells showed higher levels of caspase 3/7 activity than that of uninfected cells (FIG. 3C). Our observation suggests that ZIKV exerts oncolytic effect by apoptotic cell death during active infection. We provide the first evidence that Zika virus can be used for the treatment of the incurable glioblastoma cancer.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Further, the term "about" when used in herein connection with a referenced numeric indication is defined by context as used in the specification and claims of the application.

What is claimed is:

1. A method of treating a glioma, comprising:
    administering, via intra-tumoral delivery, intra-cerebral delivery, intracarotid delivery, intravenous delivery or subcutaneous delivery, a composition comprising a quantity of Zika virus for a multiplicity of infection (MOI) of about 1-100 or a quantity of Zika virus of about 10e3 to 10e11 to a subject in need thereof to treat the glioma.

2. The method of claim 1, wherein the Zika virus is an Asian genotype Zika virus or an African genotype Zika virus.

3. The method of claim 2, wherein the Asian genotype Zika virus comprises a genome represented by the sequence disclosed in GenBank accession number KU501215 (clinical isolate PRVABC59).

4. The method of claim 1, wherein the glioma is a glioblastoma.

5. The method of claim 1, wherein administering the composition comprises intra-tumoral delivery, intra-cerebral delivery, intracarotid delivery, or a combination thereof.

6. The method of claim 1, wherein administering the composition comprises intravenous delivery or subcutaneous delivery.

7. The method of claim 1, further comprising administering an additional brain tumor therapy.

8. A method of inducing an oncolytic effect on a brain tumor glioma, comprising:
    administering, via intra-tumoral delivery, intra-cerebral delivery, intracarotid delivery, intravenous delivery or subcutaneous delivery, a composition comprising a quantity of Zika virus for a multiplicity of infection (MOI) of about 1-100 or a quantity of Zika virus of about 10e3 to 10e11 to a subject in need thereof to induce the oncolytic effect on the brain tumor glioma.

9. The method of claim 8, wherein the Zika virus is an Asian genotype Zika virus or an African genotype virus.

10. The method of claim 9, wherein the Asian genotype Zika virus comprises a genome represented by the sequence disclosed in to GenBank accession number KU501215 (clinical isolate PRVABC59).

11. The method of claim 8, wherein the glioma is a glioblastoma.

12. The method of claim 8, wherein administering the composition comprises intra-tumoral delivery, intra-cerebral delivery, intracarotid delivery, or a combination thereof.

13. The method of claim 8, wherein administering the composition comprises intravenous delivery or subcutaneous delivery.

14. The method of claim 8, further comprising administering an additional brain tumor therapy.

15. A method of inducing an oncolytic effect on a tumor glioma, comprising:
    administering, via intra-tumoral delivery, intra-cerebral delivery, intracarotid delivery, intravenous delivery or subcutaneous delivery, a composition comprising a quantity of Zika virus for a multiplicity of infection (MOI) of about 1-100 or a quantity of Zika virus of about 10e3 to 10e11 to a subject in need thereof to induce the oncolytic effect on the glioma,
    wherein the tumor expresses a flaviviral cell entry receptor selected from the group consisting of GRP78, SDC2, HSP90AB1, TYRO2, AXL, MERTK and combinations thereof.

16. The method of claim 15, wherein the Zika virus is an Asian genotype Zika virus or an African genotype Zika virus.

17. The method of claim 16, wherein the Asian genotype Zika virus comprises a genome represented by the sequence disclosed in to GenBank accession number KU501215 (clinical isolate PRVABC59).

* * * * *

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: synthetic construct

<400> SEQUENCE: 1
ccacctttga cgctggg                                                    17

<210> SEQ ID NO 2
<211> LENGTH: 23
<212> TYPE: DNA
<213> ORGANISM: Artificial Sequence
<220> FEATURE:
<223> OTHER INFORMATION: synthetic construct

<400> SEQUENCE: 2
cataccagga aatgagcttg aca                                             23

<210> SEQ ID NO 3
<211> LENGTH: 26
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: R can be A or G
<220> FEATURE:
<221> NAME/KEY: misc_feature
<222> LOCATION: (15)..(15)
<223> OTHER INFORMATION: R can be A or G

<400> SEQUENCE: 3
aartacacat accaraacaa agtggt                                          26

<210> SEQ ID NO 4
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
```

```
<223> OTHER INFORMATION: R can be A or G
<220> FEATURE:
<221> NAME/KEY: misc_feature
<222> LOCATION: (10)..(10)
<223> OTHER INFORMATION: Y can be  C or T
<220> FEATURE:
<221> NAME/KEY: misc_feature
<222> LOCATION: (13)..(13)
<223> OTHER INFORMATION: Y can be  C or T

<400> SEQUENCE: 4
tccrctcccy ctytggtctt g                                              21
```